US006517567B2

(12) United States Patent
Bass, Jr. et al.

(10) Patent No.: US 6,517,567 B2
(45) Date of Patent: Feb. 11, 2003

(54) APPARATUS AND METHOD FOR PACIFIER WITHDRAWAL

(76) Inventors: Albert R. Bass, Jr., 813 Plum Rose Dr., Liberty, MO (US) 64068; John G. Butler, 8924 Gillette, Lenexa, KS (US) 66215

( * ) Notice: Subject to any disclaimer, the term of this patent is extended or adjusted under 35 U.S.C. 154(b) by 0 days.

(21) Appl. No.: 09/726,727

(22) Filed: Nov. 30, 2000

(65) Prior Publication Data

US 2002/0065537 A1 May 30, 2002

(51) Int. Cl.[7] .................................... A61B 17/00
(52) U.S. Cl. .................................... 606/234
(58) Field of Search .................................... 606/234, 235, 606/236; 215/11.1, 11.2, 11.3, 11.4, 11.5, 11.6

(56) References Cited

U.S. PATENT DOCUMENTS

| | | | | |
|---|---|---|---|---|
| 2,860,639 A | | 11/1958 | Hoover | |
| 3,363,630 A | | 1/1968 | Hines | |
| 3,556,104 A | | 1/1971 | Janklow | |
| 4,188,747 A | | 2/1980 | Kramer | |
| 4,192,307 A | | 3/1980 | Baer | |
| 4,878,496 A | * | 11/1989 | Chen | 606/234 |
| D318,530 S | | 7/1991 | Marriott | |
| 5,160,344 A | | 11/1992 | Werton | |
| 5,176,705 A | | 1/1993 | Noble | |
| 5,211,656 A | | 5/1993 | Maddocks et al. | |
| D337,825 S | | 7/1993 | Craner | |
| D341,891 S | | 11/1993 | Held | |
| 5,292,336 A | | 3/1994 | Spencer, Jr. et al. | |
| 5,342,398 A | | 8/1994 | Sun | |
| 5,366,481 A | * | 11/1994 | Zade | 606/234 |
| 5,391,184 A | | 2/1995 | Rosenthal | |
| D359,123 S | | 6/1995 | Perrine | |
| D395,515 S | | 6/1998 | Fletcher | |
| D413,675 S | | 9/1999 | Thorpe et al. | |
| 6,041,950 A | | 3/2000 | Soehnlein | |
| 6,066,162 A | * | 5/2000 | Hudson | 606/234 |

* cited by examiner

*Primary Examiner*—Kevin T. Truong
(74) *Attorney, Agent, or Firm*—John C. McMahon

(57) ABSTRACT

An apparatus and method for pacifier withdrawal are disclosed. The apparatus comprises a plurality of successive pacifiers wherein each pacifier has a handle, a nipple connected to said handle, and a shield interposed between the handle and the nipple. Each successive pacifier has a nipple which is shorter in length than its predecessor. The invention may be practiced as a set of complete pacifiers, as a single pacifier with interchangeable nipples, or as a single pacifier having a nipple which retracts into the handle to shorten its exposed length. The method of using the pacifier withdrawal apparatus is to provide the infant with a first pacifier having a full length nipple and to allow the infant to use the first pacifier for a specified time period in order to become accustomed to it. The first pacifier is then withdrawn and replaced with a second pacifier having a nipple which is somewhat shorter than that of the first pacifier and the infant is allowed to use the second pacifier until he or she has become accustomed to the shorter nipple. The process of withdrawing the pacifier and replacing it with one having a shorter nipple is repeated until the infant has become accustomed to a final pacifier having a nipple with a minimal length. The final pacifier is then withdrawn without replacement.

7 Claims, 2 Drawing Sheets

APPARATUS AND METHOD FOR PACIFIER WITHDRAWAL

BACKGROUND OF THE INVENTION

1. Field of the Invention

The present invention relates to the field of infant pacifiers, and more particularly to an apparatus and method for withdrawing a pacifier from an infant in stages.

2. Description of the Related Art

Infant pacifiers are well know in the art. A pacifier generally comprises an elastomeric nipple fastened to a handle with a shield interposed between the nipple and the handle. Pacifiers are used by parents in an attempt to keep an infant or small child quiet and contented between feedings. The nipple of the pacifier is inserted into the infant's mouth and the infant is allowed to suck on the nipple, the sucking action satisfying the infant's need for oral stimulation.

While usage of a pacifier has the benefit of calming an infant, prolonged usage has also been shown to cause a variety of problems. These problems include orthodontic malformations such as overbite and open bite (a vertical gap between upper and lower front teeth), and an increased incidence of ear infections. A child who continues to use a pacifier past a certain age can also experience embarrassment and social adjustment problems when dealing with his or her peers. It is therefore important that the pacifier be withdrawn from the infant before these problems can occur.

Parents often encounter difficulties when attempting to discontinue the use of a pacifier. If the pacifier is withdrawn abruptly, the child can react with extreme behavior such as crying fits and tantrums. The child may find it difficult to go to sleep without the pacifier. Abrupt removal of the pacifier can also cause the child to resort to thumb-sucking as a substitute, which can result in even more severe orthodontic problems.

It is apparent that there remains a need for an apparatus and method for gradually withdrawing a pacifier from an infant so that the negative consequences of pacifier usage can be avoided without encountering adverse behavior upon withdrawal.

SUMMARY OF THE INVENTION

The present invention comprises an apparatus and method for pacifier withdrawal. The apparatus comprises a plurality of successive pacifiers wherein each pacifier has a handle, a nipple connected to said handle, and a shield interposed between the handle and the nipple. Each successive pacifier has a nipple which is shorter in length than its predecessor. The invention may be practiced as a set of complete pacifiers, as a single pacifier with interchangeable nipples, or as a single pacifier having a nipple which retracts into the handle to shorten its exposed length.

The method of using the pacifier withdrawal apparatus is to provide the infant with a first pacifier having a full length nipple to allow the infant to use the first pacifier for a specified time period in order to become accustomed to it. The first pacifier is then withdrawn and replaced with a second pacifier having a nipple which is somewhat shorter than that of the first pacifier and the infant is allowed to use the second pacifier until he or she has become accustomed to the shorter nipple. The process of withdrawing the pacifier and replacing it with one having a shorter nipple is repeated until the infant has become accustomed to a final pacifier having a nipple with a minimal length. The final pacifier is then withdrawn without replacement.

OBJECTS AND ADVANTAGES OF THE INVENTION

The principal objects and advantages of the present invention include: providing an apparatus for withdrawing a pacifier from an infant; providing such an apparatus which allows the pacifier to be permanently withdrawn without creating adverse behavior in the infant; providing such an apparatus which allows the pacifier to be withdrawn without causing the infant to revert to thumb-sucking; providing a method of using the pacifier withdrawal apparatus; and providing such an apparatus and method which are economical to use and efficient in operation.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
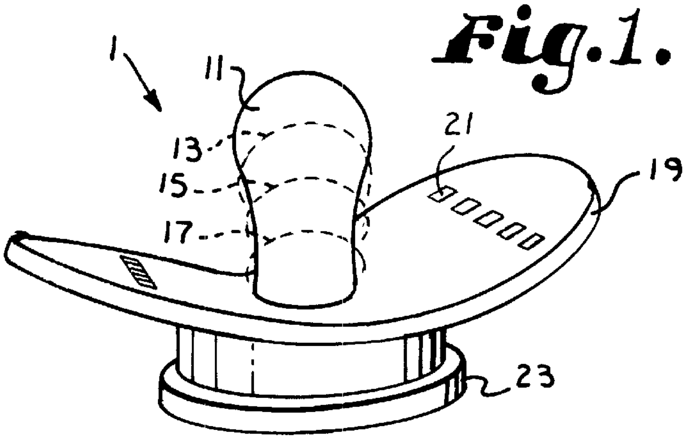
FIG. 1 is an enlarged perspective view of the pacifier withdrawal apparatus showing the sizes of the various nipples for comparison.
Figure 2:
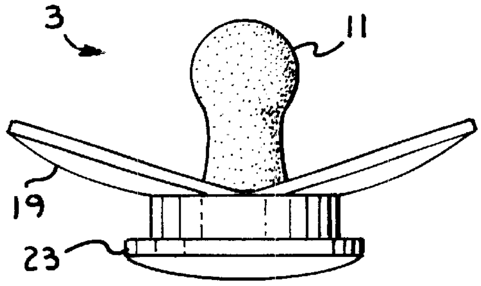
FIG. 2 is a front elevation view of the first stage pacifier with full length nipple.
Figure 3:
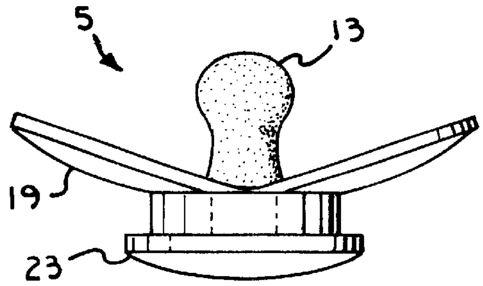
FIG. 3 is a front elevation view of a second stage pacifier with a three-quarter length nipple.
Figure 4:
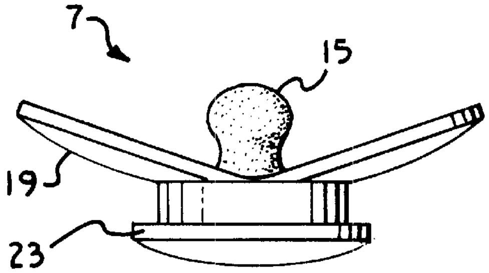
FIG. 4 is a front elevation view of a third stage pacifier with a one-half length nipple.
Figure 5:
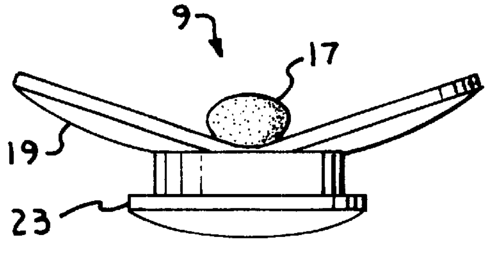
FIG. 5 is a front elevation view of the fourth stage pacifier with a one-quarter length nipple.

Referring to the drawings in more detail, the reference number 1 generally designates a pacifier withdrawal apparatus embodying the present invention. The apparatus 1 generally comprises a plurality of pacifiers, depicted herein as four pacifiers 3, 5, 7, 9. Each pacifier 3, 5, 7, 9 has a respective nipple 11, 13, 15, 17, each said nipple 11, 13, 15, 17 being progressively shorter in length than it predecessor. For example, the pacifier 3 is shown in FIG. 2 as having a one inch nipple 11, the pacifier 5 is shown in FIG. 3 as having a three-quarter inch nipple 13, the pacifier 7 is shown in FIG. 4 as having a one-half inch nipple 15, and the pacifier 9 is shown in FIG. 5 as having a one-quarter inch nipple 17.

Each pacifier 3, 5, 7, 9 is also equipped with a shield 19 having ventilation holes 21 and a handle 23. The shields 19 and handles 23 are preferably all of the same size, shape, and color to minimize any perceived difference between the pacifiers 3, 5, 7, 9 in the mind of an infant using the apparatus 1.

The apparatus 1 can be practiced in several manners, each of which is within the scope of the present invention. Applicants' preferred embodiment of the apparatus 1 is to package a plurality of complete and separate pacifiers (for example four pacifiers 3, 5, 7, 9 having respective nipples 11, 13, 15, 17) together as a set. The invention could also be practiced by providing a single pacifier handle 23 and shield 19 having removable and interchangeable nipples 11, 13, 15, 17. A third alternative would be to provide a single pacifier (not shown) having a nipple which is retractable into the handle to shorten its exposed length.

In use, the apparatus 1 is utilized to gradually eliminate an infant's desire for a pacifier by switching the infant from the pacifier 3 with its full-sized nipple 11 to successive pacifiers 5, 7, 9 with reduced sized nipples 13, 15, 17 respectively. The infant is allowed to use each pacifier 3, 5, 7, 9 for a specified time period or "stage," for example a period of one to one-and-a-half weeks.

During Stage 1 (FIG. 2) of the withdrawal process, the infant is given the pacifier 3 in place of the pacifier which he or she has been using. The infant is then allowed to become accustomed to the pacifier 3 and the nipple 11. The infant is then transitioned to the pacifier 5 with its slightly shorter nipple 13 and allowed to use the pacifier 5 during Stage 2 (FIG. 3) of the process. Because of the shorter nipple 13, the infant will probably derive slightly less pleasure from sucking on the pacifier 5 than he or she did from the pacifier 3, however the difference should not be substantial enough to cause the infant to reject the pacifier 5. The transition will be eased somewhat by the fact that the handle 23 and the shield 19 of the pacifier 5 are identical to those of the pacifier 3 and are therefore already familiar to the infant.

For Stage 3 (FIG. 4), the infant is transitioned to the pacifier 7 with its nipple 13 which is reduced in length from the previous nipple 11. Again, the difference between the nipples 13 and 11 should not be sufficient to induce extreme rejection behavior on the part of the infant, however the infant will probably experience less pleasure from the use of the pacifier 7 than was attained from the pacifier 5.

In the final stage, Stage 4 (FIG. 5), the infant is given the pacifier 9 which is equipped with the shortest nipple 15. Once again, the difference between the nipples 13 and 15 should not be significant enough to cause the infant to initially reject the pacifier 9, however the infant will probably obtain relatively little pleasure from the use of the pacifier 9 because of the short nipple 15. At the end of Stage 4, the pacifier 9 is withdrawn without replacement. Because the infant was probably not receiving a great deal of gratification from the use of the pacifier 9 anyway, the withdrawal of the pacifier 9 will not induce a hardship on the infant sufficient to induce the tantrums or crying which would have resulted had the infant's original pacifier been withdrawn without the use of the pacifier withdrawal apparatus 1. Use of the apparatus 1 will also lessen the chance that the infant will revert to thumb-sucking behavior in the absence of a pacifier because the infant's need for oral gratification has been gradually tapered off.

Figure 6:
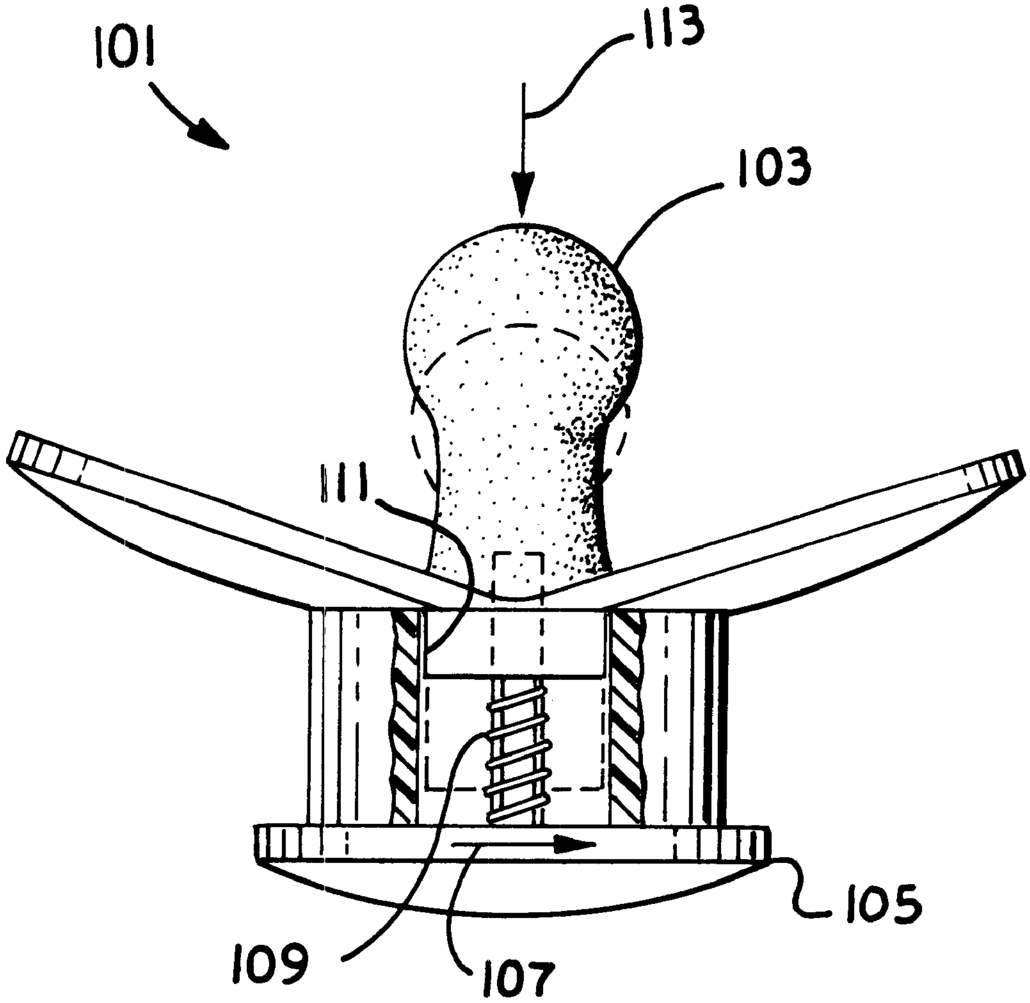
FIG. 6 is a front elevation view of a pacifier with a retractable nipple comprising a modified embodiment of the present invention, with portions broken away to reveal internal construction.

A pacifier 101 comprising a modified embodiment of the present invention is shown in FIG. 6 and includes a retractable nipple 103. The nipple 103 is retracted by turning a knob 105 in the direction indicated by the arrow 107, which rotates a screw-threaded rod 109, which is threadedly connected to the nipple 103. The base of the nipple 103 is thus retracted into a cavity 111 in the direction indicated by the down/retraction arrow 113.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for gradually curtailing pacifier use by an infant, said apparatus comprising a pacifier having a handle, a nipple connected to said handle, and means for incrementally retracting said nipple into said handle such that an exposed length of said nipple may be selectively varied in stages.

2. The apparatus as in claim 1, wherein:

a) said handle includes a cavity telescopically receiving said nipple; and b) said means for retracting comprises a rotating knob mounted on said handle and a threaded shaft fixedly mounted on said rotating knob and threadably received in said nipple for retracting and extending said nipple with respect to said cavity.

3. An apparatus for gradually curtailing pacifier use by an infant, comprising:

a) a pacifier having a handle with a cavity formed therein and a nipple telescopically received by said cavity;

b) a rotating knob mounted on said handle; and c) a threaded shaft fixedly mounted on said rotating knob and threadably received in said nipple for retracting and extending same with respect to said cavity such that said nipple is retractable into said handle to vary an exposed length of said nipple.

4. A method for gradually curtailing pacifier use by an infant, the method comprising the steps of:

a) providing a pacifier having a handle and a nipple selectively and incrementally retractable into said handle;

b) presenting said pacifier to the infant with a first exposed length of said nipple extending from said handle and allowing the infant to use said pacifier for a first time period in order to become accustomed to said first exposed length;

c) retracting said nipple relative to said handle such that a second exposed length of said nipple extends from said handle, said second exposed length being shorter than said first exposed length;

d) re-presenting said pacifier to the infant and allowing the infant to use said pacifier for a second time period in order to become accustomed to said second exposed length;

e) repeating said retracting and re-presenting steps through a plurality of progressively shorter exposed lengths of said nipple until the infant becomes accustomed to a minimal exposed length of said nipple; and f) withdrawing said pacifier without replacement.

5. The method as in claim 4, wherein each said time period is one to one-and-a-half weeks.

6. A method for gradually curtailing pacifier use by an infant, the method comprising the steps of:

a) providing a pacifier having a handle, a nipple, and means for selectively and incrementally varying an exposed length of said nipple;

b) presenting said pacifier to the infant with a first exposed length of said nipple and allowing the infant to use said pacifier for a first time period in order to become accustomed to said first exposed length;

c) decreasing said exposed length of said nipple to a second exposed length shorter than said first exposed length;

d) re-presenting said pacifier to the infant and allowing the infant to use said pacifier for a second time period in order to become accustomed to said second exposed length;

e) repeating said decreasing and re-presenting steps through a plurality of progressively shorter exposed lengths of said nipple until the infant becomes accustomed to a minimal exposed length of said nipple; and f) withdrawing said pacifier without replacement.

7. The method as in claim 6, wherein each said time period is one to one-and-a-half weeks.

* * * * *